(12) United States Patent
El-Sherbeini et al.

(10) Patent No.: US 6,949,336 B1
(45) Date of Patent: Sep. 27, 2005

(54) MURF GENE AND ENZYME OF PSEUDOMONAS AERUGINOSA

(75) Inventors: Mohamend El-Sherbeini, Westfield, NJ (US); Barbara Azzolina, Denville, NJ (US)

(73) Assignee: Merck & Co., Inc., Rahway, NJ (US)

( * ) Notice: Subject to any disclaimer, the term of this patent is extended or adjusted under 35 U.S.C. 154(b) by 279 days.

(21) Appl. No.: 10/070,778

(22) PCT Filed: Sep. 6, 2000

(86) PCT No.: PCT/US00/24437

§ 371 (c)(1),
(2), (4) Date: Mar. 7, 2002

(87) PCT Pub. No.: WO01/18018

PCT Pub. Date: Mar. 15, 2001

Related U.S. Application Data

(60) Provisional application No. 60/153,293, filed on Sep. 10, 1999.

(51) Int. Cl.[7] .................................................. C12Q 1/00
(52) U.S. Cl. .................. 435/4; 435/183; 435/320.1; 435/252.3; 435/254.11; 435/419; 435/325; 536/23.1; 536/23.2; 536/23.7
(58) Field of Search .............................. 536/23.1, 23.2, 536/23.7; 435/320.1, 252.3, 254.11, 419, 325, 183, 4

(56) References Cited

U.S. PATENT DOCUMENTS 6,551,795 B1 * 4/2003 Rubenfield et al. ........ 435/69.1

OTHER PUBLICATIONS

Lugtenberg, E. J. J., "Studies on *Escherichia coli* Enzymes Involved in the Synthesis of Uridine Diphosphate–NAcetyl-–Muramyl–Pentapeptide", Journal of Bacteriology, vol. 110, No. 1, pp. 26–34 (1972).

Mengin–Lecreulx et al., "Cytoplasmic Steps of Peptidoglycan Synthesis in *Escherichia coli*", Journal of Bacteriology, vol. 151, No. 3, pp. 1109–1117 (1982).

Kleinkauf et al., "Nonribosomal biosynthesis of peptide antibiotics", European Journal of Biochemistry, vol. 192, pp. 1–15 (1990).

Jin et al., "Structural Studies of *Escherichia coli* UDP-N–Acetyluramate:L–Alanine Ligase", Biochemistry, vol. 35, No. 5, pp. 1423–1431 (1996).

Parquet et al., "Nucleotide sequence of the *murF* gene encoding the UDP–MurNAc–pentapeptide synthetase of *Escherichia coli*", Nucleic Acids Research, vol. 17, No. 13, p. 5379 (1989).

Stover et al., GenBank, GI No. 9950633 (2000) *Pseudomonas aeruginosa* PA01, section 417 of 529 of the complete genome.

Stover et al., GenBank, GI No. 9950648 (2000) UDP-N–acetylmuramoylalanyl–D–glutamyl–2,6–diaminopinelate—D–alanyl–D–alaryl ligase.

Sanschagrin et al., "Abstracts of the 97th General Meeting of the American Society for Microbiology", p. 318 (May 1997).

Dewar et al., "*Pseudomonas aeruginosa* PAO1 Bacterial Frtificial Chromosomes: Strategies for Mapping, Screening, and Sequencing 100 kb Loci of the 5.9 Mb Genome", Microbial & Comparative Genomics, vol. 3, No. 2, pp. 105–117 (1998).

Liao et al., "Cloning and Characterization of the *Pseudomonas aeruginosa pbpB* Gene Encoding Penicillin–Binding Protein 3", Antimicrobial Agents and Chemotherapy, vol. 39, No. 8, pp. 1871–1874 (Aug. 1995).

Ikeda et al., "Homology Among MurC, MurD, MurE and MurF Proteins in *Escherichia coli* and that Between *E. coli* MurG and a Possible MurG protein in *Bacillus subtilis*", J. Gen. Appl. Microbiol., vol. 36, pp. 179–187 (1990).

* cited by examiner

*Primary Examiner*—Kathleen Kerr
(74) *Attorney, Agent, or Firm*—Yang Xu; Jack L. Tribble

(57) ABSTRACT

This invention provides isolated polynucleotides that encode the MurF (UDP-N-acetylmuramyl-L-alanine-D-glutamate-m-DaD:D-alanine-D-alanine ligase) protein of *Pseudomonas aeruginosa*. Purified and isolated MurF recombinant proteins are also provided. Nucleic acid sequences which encode functionally active MurF proteins are described. Assays for the identification of modulators of the expression of murF and inhibitors of the activity of MurF, are also provided.

13 Claims, 4 Drawing Sheets

FIG. 1A

1   ATGCTTGAGCCTCTTCGCCTCAGCCAGTTGACGGTCGCGCTGGACGCCCGCCTGATCGGC  60
    TACGAACTCGGAGAAGCGGAGTCGGTCAACTGCCAGCGCGACCTGCGGGCGGACTAGCCG

MetLeuGluProLeuArgLeuSerGlnLeuThrValAlaLeuAspAlaArgLeuIleGly

61  GAGGACGCCGTCTTTTCGGCGGTTTCCACCGACAGTCGCGCCATCGGGCCCGGCCAACTG  120
    CTCCTGCGGCAGAAAAGCCGCCAAAGGTGGCTGTCAGCGCGGTAGCCCGGGCCGGTTGAC

GluAspAlaValPheSerAlaValSerThrAspSerArgAlaIleGlyProGlyGlnLeu

121 TTCATTGCCCTGAGTGGGCCGCGTTTCGACGGCCACGACTATCTCGCCGAGGTTGCCGCC  180
    AAGTAACGGGACTCACCCGGCGCAAAGCTGCCGGTGCTGATAGAGCGGCTCCAACGGCGG

PheIleAlaLeuSerGlyProArgPheAspGlyHisAspTyrLeuAlaGluValAlaAla

181 AAGGGCGCGGTGGCTGCGCTGGTGGAGCGCGAAGTCGCCGACGCGCCCTTGCCGCAATTG  240
    TTCCCGCGCCACCGACGCGACCACCTCGCGCTTCAGCGGCTGCGCGGGAACGGCGTTAAC

LysGlyAlaValAlaAlaLeuValGluArgGluValAlaAspAlaProLeuProGlnLeu

241 CTGGTGCGCGATACCCGTGCGGCCCTGGGGCGACTGGGCGCGCTGAACCGGCGCAAGTTC  300
    GACCACGCGCTATGGGCACGCCGGGACCCCGCTGACCCGCGCGACTTGGCCGCGTTCAAG

LeuValArgAspThrArgAlaAlaLeuGlyArgLeuGlyAlaLeuAsnArgArgLysPhe

301 ACCGGCCCGCTGGCGGCCATGACGGGCTCCAGCGGCAAGACCGCGGTCAAGGAGATGCTC  360
    TGGCCGGGCGACCGCCGGTACTGCCCGAGGTCGCCGTTCTGGCGCCAGTTCCTCTACGAG

ThrGlyProLeuAlaAlaMetThrGlySerSerGlyLysThrAlaValLysGluMetLeu

361 GCCAGCATCCTGCGTACCCAGGCCGGCGATGCCGAGTCGGTGCTGGCTACCCGTGGCAAT  420
    CGGTCGTAGGACGCATGGGTCCGGCCGCTACGGCTCAGCCACGACCGATGGGCACCGTTA

AlaSerIleLeuArgThrGlnAlaGlyAspAlaGluSerValLeuAlaThrArgGlyAsn

421 CTGAACAACGACCTCGGCGTACCGCTGACCCTGCTGCAACTGGCGCCGCAGCACCGTAGC  480
    GACTTGTTGCTGGAGCCGCATGGCGACTGGGACGACGTTGACCGCGGCGTCGTGGCATCG

LeuAsnAsnAspLeuGlyValProLeuThrLeuLeuGlnLeuAlaProGlnHisArgSer

481 GCAGTGATCGAACTGGGCGCCCTCGCGCATCGGCGAGATCGCCTACACGGTCGAGCTGACC  540
    CGTCACTAGCTTGACCCGCGGAGCGCGTAGCCGCTCTAGCGGATGTGCCAGCTCGACTGG

AlaValIleGluLeuGlyAlaSerArgIleGlyGluIleAlaTyrThrValGluLeuThr

FIG. 1B

```
541  CGCCCGCACGTGGCGATCATCACCAATGCCGGAACCGCCCATGTCGGCGAGTTCGGCGGA  600
     GCGGGCGTGCACCGCTAGTAGTGGTTACGGCCTTGGCGGGTACAGCCGCTCAAGCCGCCT
      ^    *    ^    *    ^    *    ^    *    ^    *    ^    *
     ArgProHisValAlaIleIleThrAsnAlaGlyThrAlaHisValGlyGluPheGlyGly

601  CCGGAGAAGATCGTCGAGGCGAAGGGCGAGATACTCGAAGGGCTGGCCGCCGACGGCACC  660
     GGCCTCTTCTAGCAGCTCCGCTTCCCGCTCTATGAGCTTCCCGACCGGCGGCTGCCGTGG
      ^    *    ^    *    ^    *    ^    *    ^    *    ^    *
     ProGluLysIleValGluAlaLysGlyGluIleLeuGluGlyLeuAlaAlaAspGlyThr

660  GCCGTACTGAACCTGGACGACAAGGCCTTCGACACCTGGAAGGCCCGTGCCAGCGGCCGT  720
     CGGCATGACTTGGACCTGCTGTTCCGGAAGCTGTGGACCTTCCGGGCACGGTCGCCGGCA
      ^    *    ^    *    ^    *    ^    *    ^    *    ^    *
     AlaValLeuAsnLeuAspAspLysAlaPheAspThrTrpLysAlaArgAlaSerGlyArg

721  CCGTTGCTGACTTTCTCCCTCGACCGGCCCCAGGCCGATTTCCGCGCCGCCGATCTGCAG  780
     GGCAACGACTGAAAGAGGGAGCTGGCCGGGGTCCGGCTAAAGGCGCGGCGGCTAGACGTC
      ^    *    ^    *    ^    *    ^    *    ^    *    ^    *
     ProLeuLeuThrPheSerLeuAspArgProGlnAlaAspPheArgAlaAlaAspLeuGln

781  CGCGATGCGCGCGGCTGCATGGGCTTCAGGCTGCAGGGCGTAGCGGGTGAAGCGCAGGTC  840
     GCGCTACGCGCGCCGACGTACCCGAAGTCCGACGTCCCGCATCGCCCACTTCGCGTCCAG
      ^    *    ^    *    ^    *    ^    *    ^    *    ^    *
     ArgAspAlaArgGlyCysMetGlyPheArgLeuGlnGlyValAlaGlyGluAlaGlnVal

841  CAGCTCAACCTGCTGGGGCGGCACAATGTCGCCAATGCCCTGGCTGCGGCCGCTGCCGCC  900
     GTCGAGTTGGACGACCCCGCCGTGTTACAGCGGTTACGGGACCGACGCCGGCGACGGCGG
      ^    *    ^    *    ^    *    ^    *    ^    *    ^    *
     GlnLeuAsnLeuLeuGlyArgHisAsnValAlaAsnAlaLeuAlaAlaAlaAlaAlaAla

901  CATGCACTGGGCGTGCCGCTGGATGGGATCGTCGCCGGGCTGCAGGCGCTGCAGCCGGTC  960
     GTACGTGACCCGCACGGCGACCTACCCTAGCAGCGGCCCGACGTCCGCGACGTCGGCCAG
      ^    *    ^    *    ^    *    ^    *    ^    *    ^    *
     HisAlaLeuGlyValProLeuAspGlyIleValAlaGlyLeuGlnAlaLeuGlnProVal

961  AAGGGCCGCGCGGTAGCGCAACTGACCGCCAGCGGGCTGCGTGTGATAGACGACAGCTAC  1020
     TTCCCGGCGCGCCATCGCGTTGACTGGCGGTCGCCCGACGCACACTATCTGCTGTCGATG
      ^    *    ^    *    ^    *    ^    *    ^    *    ^    *
     LysGlyArgAlaValAlaGlnLeuThrAlaSerGlyLeuArgValIleAspAspSerTyr

1021 AACGCCAACCCCGCGTCAATGCTGGCGGCGATTGATATACTGAGCGGCTTTTCCGGGCGC  1080
     TTGCGGTTGGGGCGCAGTTACGACCGCCGCTAACTATATGACTCGCCGAAAAGGCCCGCG
      ^    *    ^    *    ^    *    ^    *    ^    *    ^    *
     AsnAlaAsnProAlaSerMetLeuAlaAlaIleAspIleLeuSerGlyPheSerGlyArg
```

FIG. 1C

```
1081 ACCGTCCTGGTCCTCGGAGACATGGGCGAACTCGGTTCCTGGGCCGAGCAGGCCCACCGC 1140
     TGGCAGGACCAGGAGCCTCTGTACCCGCTTGAGCCAAGGACCCGGCTCGTCCGGGTGGCG
     ThrValLeuValLeuGlyAspMetGlyGluLeuGlySerTrpAlaGluGlnAlaHisArg

1141 GAGGTGGGCGCCTACGCCGCTGGCAAGGTGTCCGCGCTCTATGCGGTCGGACCGCTGATG 1200
     CTCCACCCGCGGATGCGGCGACCGTTCCACAGGCGCGAGATACGCCAGCCTGGCGACTAC
     GluValGlyAlaTyrAlaAlaGlyLysValSerAlaLeuTyrAlaValGlyProLeuMet

1201 GCCCACGCCGTACAGGCGTTCGGCGCCACGGGCCGGCACTTCGCCGACCAGGCCAGCCTG 1260
     CGGGTGCGGCATGTCCGCAAGCCGCGGTGCCCGGCCGTGAAGCGGCTGGTCCGGTCGGAC
     AlaHisAlaValGlnAlaPheGlyAlaThrGlyArgHisPheAlaAspGlnAlaSerLeu

1261 ATCGGGGCGCTGGCCACCGAACAACCGACAACCACCATTTTGATCAAGGGTTCCCGCAGT 1320
     TAGCCCCGCGACCGGTGGCTTGTTGGCTGTTGGTGGTAAAACTAGTTCCCAAGGGCGTCA
     IleGlyAlaLeuAlaThrGluGlnProThrThrThrIleLeuIleLysGlySerArgSer

1321 GCGGCGATGGACAAAGTCGTCGCGGCGCTGTGCGGTTCCTCCGAGGAGAGTCACTAATGC 1380
     CGCCGCTACCTGTTTCAGCAGCGCCGCGACACGCCAAGGAGGCTCCTCTCAGTGATTACG
     AlaAlaMetAspLysValValAlaAlaLeuCysGlySerSerGluGluSerHis

1381 TCCTGCTGCTGGC 1440
     AGGACGACGACCG
```

US 6,949,336 B1

MURF GENE AND ENZYME OF PSEUDOMONAS AERUGINOSA

CROSS-REFERENCE TO RELATED APPLICATIONS

This application claims benefit of provisional 60/153,293 filed Sep. 10, 1999

STATEMENT REGARDING FEDERALLY-SPONSORED R&D

Not applicable.

REFERENCE TO MICROFICHE APPENDIX

Not applicable.

FIELD OF THE INVENTION

This invention relates to the genes and enzymes involved in cell wall synthesis in bacteria, and particularly to the inhibition of such enzymes.

BACKGROUND OF THE INVENTION

The pathway of peptidoglycan biosynthesis is both essential and unique to bacteria, making it an attractive target for antibiotic research. Several enzymes in this pathway are molecular targets of naturally occurring antibiotics such as fosfomycin, cycloserine, b-lactams and vancomycin.

The construction of the peptidoglycan begins in the cytoplasm with an activated sugar molecule, UDP-N-acetylglucosamine. After two reactions (catalyzed by MurA and MurB) that result in the placement of a lactyl group on the 3—OH of the glucosamine moiety, a series of ATP-dependent amino acid ligases (MurC, -D, -E, and —F) catalyze the stepwise synthesis of the pentapeptide sidechain using the newly synthesized lactyl carboxylate as the first acceptor site. After attachment of the sugar pentapeptide to a lipid carrier in the plasma membrane, another glucosamine unit is added to the 4—OH of the muramic acid moiety. The completed monomeric building block is moved across the membrane into the periplasm where the penicillin-binding proteins enzymatically add it into the growing cell wall (Lugtenberg, E. J., 1972, Studies on *Escherichia coli* enzymes involved in the synthesis of Uridine Diphosphate-N-Acetyl-Muramyl-pentapeptide. J. Bacteriol. 110:2634; Mengin-Lecreulx, D., B. Flouret, and J. van Heijenoort, 1982, Cytoplasmic steps of peptidoglycan synthesis in *Escherichia coli*. J. Bacteriol. 151: 1109–1117).

Because the pentapeptide sidechain is not synthesized ribosomally it contains more diverse chemical functionality than a typical peptide, both structurally and stereochemically. Two of the enzymes catalyze the addition of D-amino acids (MurD and MurF) and MurE mediates the formation of a peptide bond between the g-carboxylate of D-glutamate and the amino group of L-lysine. Presumably these structures render the exposed peptidoglycan resistant to the action of proteases, but they also imply that the active sites of the enzymes must have unusual structures in order to handle the somewhat uncommon substrates. These unusual active sites are targets to bind novel inhibitors that can have antimicrobial activity.

Although peptidoglycan assembly is a proven target for antibiotics, there are no known inhibitors for many of the enzymes of the pathway. Since these enzymes are conserved among eubacteria, inhibitors of this pathway are likely to be broad spectrum antibiotics. Among these potential enzyme targets is MurF, UDP-N-acetylmuramyl-L-alanine-D-Glutamine-m-Dap: D-alanine-D-alanine ligase. This enzyme is a target for the antibiotic cycloserine (Kleinkauf H and H. von Dohren. 1990. Nonribosomal biosynthesis of peptide antibiotics. Eur J. Biochem. 192:1–15). This validates the assumption that inhibitors of this enzyme are likely to lead to antibiotics for treating infections with either Gram (−ve) or Gram (+ve) bacteria.

SUMMARY OF THE INVENTION

Polynucleotides and polypeptides of *Pseudomonas aeruginosa* MurF, an enzyme involved in bacterial cell wall biosynthesis are provided. The recombinant MurF enzyme is catalytically active in ATP-dependent D-alanine-D-alanine addition reactions. The enzyme is used in in vitro assays to screen for antibacterial compounds that target cell wall biosynthesis. The invention includes the polynucleotides, proteins encoded by the polynucleotides, and host cells expressing the recombinant enzyme, probes and primers, and the use of these molecules in assays.

An aspect of this invention is a polynucleotide having a sequence encoding a *Pseudomonas aeruginosa* MurF protein, or a complementary sequence. In a particular embodiment the encoded protein has a sequence corresponding to SEQ ID NO:2. In other embodiments, the encoded protein can be a naturally occurring mutant or polymorphic form of the protein. In preferred embodiments the polynucleotide can be DNA, RNA or a mixture of both, and can be single or double stranded. In particular embodiments, the polynucelotide is comprised of natural, non-natural or modified nucleotides. In some embodiments, the internucleotide linkages are linkages that occur in nature. In other embodiments, the internucleotide linkages can be non-natural linkages or a mixture of natural and non-natural linkages. In a most preferred embodiment, the polynucleotide has a sequence shown in SEQ ID NO:1.

An aspect of this invention is a polynucleotide having a sequence of at least about 25 contiguous nucleotides that is specific for a naturally occurring polynucleotide encoding a *Pseudomonas aeruginosa* MurF protein. In particular preferred embodiments, the polynucleotides of this aspect are useful as probes for the specific detection of the presence of a polynucleotide encoding a *Pseudomonas aeruginosa* MurF protein. In other particular embodiments, the polynucleotides of this aspect are useful as primers for use in nucleic acid amplification based assays for the specific detection of the presence of a polynucleotide encoding a *Pseudomonas aeruginosa* MurF protein. In preferred embodiments, the polynucleotides of this aspect can have additional components including, but not limited to, compounds, isotopes, proteins or sequences for the detection of the probe or primer.

An aspect of this invention is an expression vector including a polynucleotide encoding a *Pseudomonas aeruginosa* MurF protein, or a complementary sequence, and regulatory regions. In a particular embodiment the encoded protein has a sequence corresponding to SEQ ID NO:2. In particular embodiments, the vector can have any of a variety of regulatory regions known and used in the art as appropriate for the types of host cells the vector can be used in. In a most preferred embodiment, the vector has regulatory regions appropriate for the expression of the encoded protein in gram-negative prokaryotic host cells. In other embodiments, the vector has regulatory regions appropriate for expression of the encoded protein in gram-positive host cells, yeasts, *cyanobacteria* or actinomycetes. In some preferred embodiments the regulatory regions provide for inducible expression while in other preferred embodiments the regulatory regions provide for constitutive expression. Finally, according to this aspect, the expression vector can be derived from a plasmid, phage, virus or a combination thereof.

An aspect of this invention is host cell comprising an expression vector including a polynucleotide encoding a *Pseudomonas aeruginosa* MurF protein, or a complementary sequence, and regulatory regions. In a particular embodiment the encoded protein has a sequence corresponding to SEQ ID NO:2. In preferred embodiments, the host cell is a yeast, gram-positive bacterium, cyanobacterium or actinomycete. In a most preferred embodiment, the host cell is a gram-negative bacterium.

An aspect of this invention is a process for expressing a MurF protein of *P. aeruginosa* in a host cell. In this aspect a host cell is transformed or transfected with an expression vector including a polynucleotide encoding a *Pseudomonas aeruginosa* MurF protein, or a complementary sequence. According to this aspect, the host cell is cultured under conditions conducive to the expression of the encoded MurF protein. In particular embodiments the expression is inducible or constitutive. In a particular embodiment the encoded protein has a sequence corresponding to SEQ ID NO:2.

An aspect of this invention is a purified polypeptide having an amino acid sequence of SEQ ID NO:2 or the sequence of a naturally occurring mutant or polymorphic form of the protein.

An aspect of this invention is a method of determining whether a candidate compound can inhibit the activity of a *P. aeruginosa* MurF polypeptide. According to this aspect a polynucleotide encoding the polypeptide is used to construct an expression vector appropriate for a particular host cell. The host cell is transformed or transfected with the expression vector and cultured under conditions conducive to the expression of the MurF polypeptide. The cell is contacted with the candidate. Finally, one measures the activity of the MurF polypeptide in the presence of the candidate. If the activity is lower relative to the activity of the protein in the absence of the candidate, then the candidate is a inhibitor of the MurF polypeptide. In preferred embodiments, the polynucleotide encodes a protein having an amino acid sequence of SEQ ID NO:2 or a naturally occurring mutant of polymorphic form thereof. In other preferred embodiments, the polynucleotide has the sequence of SEQ ID NO:1. In particular embodiments, the relative activity of MurF is determined by comparing the activity of the MurF in a host cell. In some embodiments, the host cell is disrupted and the candidate is contacted to the released cytosol. In other embodiments, the cells can be disrupted contacting with the candidate and before determining the activity of the MurF protein. Finally, according to this aspect the relative activity can determined by comparison to a previously measured or expected activity value for the MurF activity in the host under the conditions. However, in preferred embodiments, the relative activity is determined by measuring the activity of the MurF in a control cell that was not contacted with a candidate compound. In particular embodiments, the host cell is a pseudomonad and the protein inhibited is the MurF produced by the pseudomonad.

An aspect of this invention is a compound that is an inhibitor of a *P. aeruginosa* MurF protein an assay described herein. In preferred embodiments, the compound is an inhibitor of a *P. aeruginosa* MurF protein produced by a host cell comprising an expression vector of this invention. In most preferred embodiments, the compound is also an inhibitor of MurF protein produced by a pathogenic strain *P. aeruginosa* and also inhibits the growth of said pseudomonad.

An aspect of this invention is a pharmaceutical preparation that includes an inhibitor of *P. aeruginosa* MurF and a pharmaceutically acceptable carrier.

An aspect of this invention is a method of treatment comprising administering a inhibitor of the *P. aeruginosa* MurF to a patient. The treatment can be prophylactic or therapeutic. In preferred embodiments, the appropriate dosage for a particular patient is determined by a physician.

By "about" it is meant within approximately 10–20% greater or lesser than particularly stated.

As used herein an "inhibit r" is a compound that interacts with and inhibits or prevents a polypeptide of MurF from catalyzing the ATP-dependent addition of D-alanine-D-alanine to an m-Dap residue of the UDP-N-acetylmuramyl-L-alanine-D-Glutamine-m-Dap.

As used herein a "modulator" is a compound that interacts with an aspect of cellular biochemistry to effect an increase or decrease in the amount of a polypeptide of MurF present in, at the surface or in the periplasm of a cell, or in the surrounding serum or media. The change in amount of the MurF polypeptide can be mediated by the effect of a modulator on the expression of the protein, e.g., the transcription, translation, post-translational processing, translocation or folding of the protein, or by affecting a component(s) of cellular biochemistry that directly or indirectly participates in the expression of the protein. Alternatively, a modulator can act by accelerating or decelerating the turnover of the protein either by direct interaction with the protein or by interacting with another component(s) of cellular biochemistry which directly or indirectly effects the change.

All of the references cited herein are incorporated by reference in their entirety as background material.

BRIEF DESCRIPTION OF THE DRAWINGS

FIGS. 1A–1C. Nucleotide sequence (SEQ ID NO:1) and the predicted amino acid sequence (SEQ ID NO:2) of *P. aeruginosa* murF. The amino acid sequence (SEQ ID NO:2) is presented in three-letter code below the nucleotide sequence (nucleotides 57 to 1431 of SEQ ID NO:1).

DETAILED DESCRIPTION OF THE INVENTION

Figure 2:
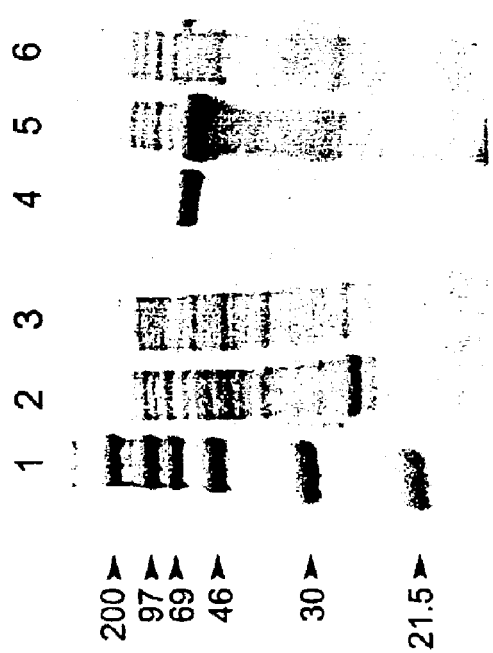
FIG. 2. Production of MurF Protein. Lane 1, Molecular weight markers; Lane2, IPTG-induced lysate of cells (BL21 (DE3)/pLysS) containing the control vector pET -15b; Lane 3, uninduced cell lysate containing the control vector pET-15b; lane 4, column-purified MurF; Lane 5 IPTG-induced lysate of cells expressing MurF; Lane 6, uninduced lysate of cells containing murF.

This invention provides polynucleotides and polypeptides of a cell wall biosynthesis gene from *Pseudomonas aeruginosa*, referred to herein as MurF. The polynucleotides and polypeptides are used to further provide expression vectors, host cells comprising the vectors, probes and primers, antibodies against the MurF protein and polypeptides thereof, assays for the presence or expression of MurF and assays for the identification of modulators and inhibitors of MurF.

Bacterial MurF, UDP-N-acetylmuramyl-L-alanine-D-glutamate-m-Dap:D-alanine-D-alanine ligase, a cytoplasmic peptidoglycan biosynthetic enzyme, catalyzes the ATP-dependent addition of D-alanine-D-alanine to the m-Dap residue of the UDP-N-acetylmuramyl-L-alanine-D-Glutamine-m-Dap precursor generating the pentapeptide UDP-N-acetylmuramyl-L-alanine-D-Glutamine-m-Dap-D-alanine-D-alanine.

N The murF gene was cloned from *Pseudomonas aeruginosa*. Sequence analysis of the *P. aeruginosa* murF gene revealed an open reading frame of 458 amino acids. The deduced amino acid sequence of *P. aeruginosa* MurF is homologous to MurF from *Escherichia coli*, *Bacillus subtilis* and other bacteria. Recombinant MurF protein from *P. aeruginosa* was over-produced as His-tagged fusion protein in *Escherichia coli* host cells and the enzyme was purified to apparent homogeneity. The recombinant enzyme catalyzed the ATP-dependent addition of D-alanine-D-alanine to the UDP-N-acetylmuramyl-L-alanine-D-Glutamine-m-Dap precursor.

Nucleic acids encoding murF from *Pseudomonas aeruginosa* are useful in the expression and production of the *P. aeruginosa* MurF protein. The nucleic acids are also useful in providing probes for detecting the presence of *P. aeruginosa* murF.

Polynucleotides

Polynucleotides useful in the present invention include those described herein and those that one of skill in the art will be able to derive therefrom following the teachings of this specification. A preferred aspect of the present invention is an isolated nucleic acid encoding a MurF protein of *Pseudomonas aeruginosa*. A preferred embodiment is a nucleic acid having the sequence disclosed in FIG. 1, SEQ ID NO:1 and disclosed as follows:

TCCGTTCTCC GACATCGAGC AGGCCGAGCG CGCCCTGGCC GCCTGGGAGG
TGCCGATCG TTGAGCCTCT TCGCCTCAGC CAGTTGACGG TCGCGCTGGA
CGCCCGCCTG ATCGGCGAGG ACGCCGTCTT TTCGGCGGTT TCCACCGACA
GTCGCGCCAT CGGGCCCGGC CAACTGTTCA TTGCCCTGAG TGGGCCGCGT
TTCGACGGCC ACGACTATCT CGCCGAGGTT GCCGCCAAGG GCGCGGTGGC
TGCGCTGGTG GAGCGCGAAG TCGCCGACGC GCCCTTGCCG CAATTGCTGG
TGCGCGATAC CCGTGCGGCC CTGGGGCGAC TGGGCGCGCT GAACCGGCGC
AAGTTCACCG GCCCGCTGGC GGCCATGACG GGCTCCAGCG GCAAGACCGC
GGTCAAGGAG ATGCTCGCCA GCATCCTGCG TACCCAGGCC GGCGATGCCG
AGTCGGTGCT GGCTACCCGT GGCAATCTGA ACAACGACCT CGGCGTACCG
CTGACCCTGC TGCAACTGGC GCCGCAGCAC CGTAGCGCAG TGATCGAACT
CGCACGTGGC GATCATCACC AATGCCGGAA CCGCCATGT CGGCGAGTTC
GGCGGACCGG AGAAGATCGT CGAGGCGAAG GGCGAGATAC TCGAAGGGCT
GGCCGCCGAC GGCACCGCCG TACTGAACCT GGACGACAAG GCCTTCGACA
CCTGGAAGGC CCGTGCCAGC GGCCGTCCGT TGCT-GACTTT CTCCCTCGAC
CGGCCCCAGG CCGATTTCCG CGCCGCCGAT CTGCAGCGCG ATGCGCGCGG
CTGCATGGGC TTCAGGCTGC AGGGCGTAGC GGGTGAAGCG CAGGTCCAGC
TCAACCTGCT GGGGCGGCAC AATGTCGCCA ATGCCCTGGC TGCGGCCGCT
GCCGCCCATG CACTGGGCGT GCCGCTGGAT GGGATCGTCG CCGGGCTGCA
GGCGCTGCAG CCGGTCAAGG GCCGCGCGGT AGCGCAACTG ACCGCCAGCG
GGCTGCGTGT GATAGACGAC AGCTACAACG CCAACCCCGC GTCAATGCTG
GCGGCGATTG ATATACTGAG CGGCTTTTCC GGGCGCACCG TCCTGGTCCT
CGGAGACATG GGCGAACTCG GTTCCTGGGC CGAGCAGGCC CACCGCGAGG
TGGGCGCCTA CGCCGCTGGC AAGGTGTCCG CGCTCTATGC GGTCGGACCG
CTGATGGCCC ACGCCGTACA GGCGTTCGGC GCCACGGGCC GGCACTTCGC
CGACCAGGCC AGCCTGATCG GGGCGCTGGC CACCGAACAA CCGACAACCA
CCATTTTGAT CAAGGGTTCC CGCAGTGCGG CGATGGACAA AGTCGTCGCG
GCGCTGTGCG GTTCCTCCGA GGAGAGTCAC TATGCTCCT GCTGCTGGC (SEQ ID NO:1)

The translation initiation and termination codons are underlined.

The isolated nucleic acid molecule of the present invention can include a ribonucleic or deoxyribonucleic acid molecule, which can be single (coding or noncoding strand) or double stranded, as well as synthetic nucleic acid, such as a synthesized, single stranded polynucleotide.

The present invention also relates to recombinant vectors and recombinant hosts, both prokaryotic and eukaryotic, which contain the substantially purified nucleic acid molecules disclosed throughout this specification.

As used herein a "polynucleotide" is a nucleic acid of more than one nucleotide. A polynucleotide can be made up of multiple polynucleotide units that are referred to by description of the unit. For example, a polynucleotide can comprise within its bounds a polynucleotide(s) having a coding sequence(s), a polynucleotide(s) that is a regulatory region(s) and/or other polynucleotide units commonly used in the art.

An "expression vector" is a polynucleotide having regulatory regions operably linked to a coding region such that, when in a host cell, the regulatory regions can direct the expression of the coding sequence. The use of expression vectors is well known in the art. Expression vectors can be used in a variety of host cells and, therefore, the regulatory regions are preferably chosen as appropriate for the particular host cell.

A "regulatory region" is a polynucleotide that can promote or enhance the initiation or termination of transcription or translation of a coding sequence. A regulatory region includes a sequence that is recognized by the RNA polymerase, ribosome, or associated transcription or translation initiation or termination factors of a host cell. Regulatory regions that direct the initiation of transcription or translation can direct constitutive or inducible expression of a coding sequence.

Polynucleotides of this invention contain full length or partial length sequences of the MurF gene sequences disclosed herein. Polynucleotides of this invention can be single or double stranded. If single stranded, the polynucleotides can be a coding, "sense," strand or a complementary, "antisense," strand. Antisense strands can be useful as modulators of the gene by interacting with RNA encoding the MurF protein. Antisense strands are preferably less than full length strands having sequences unique or specific for RNA encoding the protein.

The polynucleotides can include deoxyribonucleotides, ribonucleotides or mixtures of both. The polynucleotides can be produced by cells, in cell-free biochemical reactions or through chemical synthesis. Non-natural or modified nucleotides, including inosine, methylcytosine, deazaguanosine, etc., can be present. Natural phosphodiester internucleotide linkages can be appropriate. However, polynucleotides can have non-natural linkages between the nucleotides. Non-natural linkages are well known in the art and include, without limitation, methylphosphonates, phosphorothioates, phosphorodithioates, phosphoroamidites and phosphate ester linkages. Dephospho-linkages are also known, as bridges between nucleotides. Examples of these include siloxane, carbonate, carboxymethyl ester, acetamidate, carbamate, and thioether bridges. "Plastic DNA," having, for example, N-vinyl, methacryloxyethyl, methacryamide or ethyleneimine internucleotide linkages, can be used. "Peptide Nucleic Acid" (PNA) is also useful and resists degradation by nucleases. These linkages can be mixed in a polynucleotide.

As used herein, "purified" and "isolated" are utilized interchangeably to stand for the proposition that the polynucleotide, protein and polypeptide, or respective fragments thereof in question have been removed from the in vivo environment so that they exist in a form or purity not found in nature. Purified or isolated nucleic acid molecules can be manipulated by the skilled artisan, such as but not limited to sequencing, restriction digestion, site-directed mutagenesis, and subcloning into expression vectors for a nucleic acid fragment as well as obtaining the wholly or partially purified protein or protein fragment so as to afford the opportunity to generate polyclonal antibodies, monoclonal antibodies, or perform amino acid sequencing or peptide digestion. Therefore, the nucleic acids claimed herein can be present in whole cells or in cell lysates or in a partially or substantially purified form. It is preferred that the molecule be present at a concentration at least about five-fold to ten-fold higher than that found in nature. A polynucleotide is considered substantially pure if it is obtained purified from cellular components by standard methods at a concentration of at least about 100-fold higher than that found in nature. A polynucleotide is considered essentially pure if it is obtained at a concentration of at least about 1000-fold higher than that found in nature. We most prefer polynucleotides that have been purified to homogeneity, that is, at least 10,000–100,000 fold. A chemically synthesized nucleic acid sequence is considered to be substantially purified when purified from its chemical precursors by the standards stated above.

Included in the present invention are assays that employ further novel polynucleotides that hybridize to *P.aeruginosa* murf sequences under stringent conditions. By way of example, and not limitation, a procedure using conditions of high stringency is as follows: Prehybridization of filters containing DNA is carried out for 2 hr. to overnight at 65° C. in buffer composed of 6×SSC, 5× Denhardt's solution, and 100 μg/ml denatured salmon sperm DNA. Filters are hybridized for 12 to 48 hrs at 65° C. in prehybridization mixture containing 100 μg/ml denatured salmon sperm DNA and 5–20×10⁶ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography.

Other procedures using conditions of high stringency would include either a hybridization step carried out in 5×SSC, 5× Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook, et al., 1989, *Molecular Cloning*: A Laboratory Manual, second edition, Cold Spring Harbor Laboratory Press. In addition to the foregoing, other conditions of high stringency which may be used are well known in the art.

Polypeptides

A preferred aspect of the present invention is a substantially purified form of the MurF protein from *Pseudomonas aeruginosa*. A preferred embodiment is a protein that has the amino acid sequence which is shown in FIG. 1, in SEQ ID NO:2 and disclosed as follows:

MetLeuGluProLeuArgLeuSerGln-
LeuThrValAlaLeuAspAlaArgLeuIleGly GluAspAlaVal-
PheSerAlaValSerThrAspSerArgAlaIeGlyProGlyGlnLeu
PheIleAlaLeuserGlyProArg-
PheAspGlyHisAspTyrLeuAlaGluvalAlaAla LysGlyAla-
ValAlaAlaLeuValGluArgGluValA-
laAspAlaProLeuProGlnLeu
LeuValArgAspThrArgAlaAlaLeuG-
lyArgLeuGlyAlaLeuAsnArgArgLysPhe ThrGlyPro-
LeuAlaAlaMetThrGlySerSerG-
lyLysThrAlaValLysGluMetLeu
AlaSerIleLeuArgThrGlnAlaGl-
yAspAlaGluSerValLeuAlaThrArgGlyAsn LeuAsnAs-
nAspLeuGlyValProLeuThr-
LeuLeuGlnLeuAlaProGlnHisArgser
AlaValIleGluLeuGlyAlaSerArgI-
leGlyGluIleAlaTyrThrValGluLeuThr ArgProHisvalA-
laIleIleThrAsnAlaGlyThrAlaHisValGlyGluPheGlyGly
ProGluLysIleValGluAlaLysGly-
GluIleLeuGluGlyLeuAlaAlaAspGlyThr AlaValLeuAsn-
LeuAspAspLysAlaPheAspThrTr-
pLysAlaArgAlaSerGlyArg
ProLeuLeuThrPheSerLeuAspArg-
ProGlnAlaAspPheArgAlaAlaAspLeuGln ArgAspAl-
aArgGlyCysMetGlyPheAr-
gLeuGlnGlyValAlaGlyGluAlaGlnVal
GlnLeuAsnLeuLeuGlyArgHisAsn-
ValAlaAsnAlaLeuAlaAlaAlaAlaAlaAla HiSAlaLeuGly-
ValProLeuAspGlyIleValAlaGlyLeuGlnAlaLeuGlnProVal
LysGlyArgA laValAlaGlnLeuThrAlaSerG-
lyLeuArgValIleAspAspSerTyr AsnAlaAsnProAlaSer-
MetLeuAlaAlaIleAspIleLeuSerGlyPheSerGlyArg Thr-
ValLeuValLeuGlyAspMetGlyGluLeuGlySerTrpAlaGlu
GlnAlaHisArg GluValGlyAlaTyrAlaAlaGlyLys-
ValSerAlaLeuTyrAlaValGlyProLeuMet AlaHisAlaVal-
GlnAlaPheGlyAlaThrGlyArgHis-
PheAlaAspGlnAlaSerLeu
IleGlyAlaLeuAlaThrGluGlnPro-
ThrThrThrIleLeuIleLysGlySerArgser AlaAlaMetAs-
pLysValValAlaAlaLeuCysGlySerSerGluGluSerHis (SEQ ID NO:2)

The present invention also relates to biologically active fragments and mutant or polymorphic forms of MurF polypeptide sequence as set forth as SEQ ID NO: 2, including but not limited to amino acid substitutions, deletions, additions, amino terminal truncations and carboxy-terminal truncations such that these mutations provide for proteins or protein fragments of diagnostic, therapeutic or prophylactic use and would be useful for screening for modulators, and/or inhibitors of MurF function.

Using the disclosure of polynucleotide and polypeptide sequences provided herein to isolate polynucleotides encoding naturally occurring forms of MurF, one of skill in the art can determine whether such naturally occurring forms are mutant or polymorphic forms of MurF by sequence comparison. One can further determine whether the encoded protein, or fragments of any MurF protein, is biologically active by routine testing of the protein of fragment in a in vitro or in vivo assay for the biological activity of the MurF protein. For example, one can express N-terminal or C-terminal truncations, or internal additions or deletions, in host cells and test for their ability to catalyze the ATP-dependent addition of D-alanine-D-alanine to the UDP-N-acetylmuramyl-L-alanine-D-Glutamine-m-Dap precursor.

It is known that there is a substantial amount of redundancy in the various codons which code for specific amino acids. Therefore, this invention is also directed to those DNA sequences comprising RNA comprising alternative codons which code for the eventual translation of the identical amino acid Therefore, the present invention discloses codon redundancy which can result in different DNA molecules encoding an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide. However, any given change can be examined for any effect on biological function by simply assaying for the ability to catalyze the ATP-dependent addition of D-alanine-D-alanine to the UDP-N-acetylmuramyl-L-alanine-D-Glutamine-m-Dap precursor as compared to an unaltered MurF protein.

It is known that DNA sequences coding for a peptide can be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate.

As used herein, a "biologically active equivalent" or "functional derivative" of a wild-type MurF possesses a biological activity that is substantially similar to the biological activity of a wild type MurF. The term "functional derivative" is intended to include the "fragments," "mutants," "variants," "degenerate variants," "analogs," "orthologues," and "homologues" and "chemical derivatives" of a wild type MurF protein that can catalyze the ATP-dependent addition of D-alanine-D-alanine to the UDP-N-acetylmuramyl-L-alanine-D-Glutamine-m-Dap precursor. The term "fragment" refers to any polypeptide subset of wild-type MurF. The term "mutant" is meant to refer to a molecule that may be substantially similar to the wild-type form but possesses distinguishing biological characteristics. Such altered characteristics include but are in no way limited to altered substrate binding, altered substrate affinity and altered sensitivity to chemical compounds affecting biological activity of the MurF or MurF functional derivative. The term "variant" refers to a molecule substantially similar in structure and function to either the entire wild-type protein or to a fragment thereof. A molecule is "substantially similar" to a wild-type MurF-like protein if both molecules have substantially similar structures or if both molecules possess similar biological activity. Therefore, if the two molecules possess substantially similar activity, they are considered to be variants even if the exact structure of one of the molecules is not found in the other or even if the two amino acid sequences are not identical. The term "analog" refers to a molecule substantially similar in function to either the full-length MurF protein or to a biologically active fragment thereof.

As used herein in reference to a MurF gene or encoded protein, a "polymorphic" MurF is a MurF that is naturally found in the population of *Pseudomonads* at large. A polymorphic form of MurP can be encoded by a different nucleotide sequence from the particular murF gene disclosed herein as SEQ ID NO:1. However, because of silent mutations, a polymorphic murF gene can encode the same or different amino acid sequence as that disclosed herein. Further, some polymorphic forms MurF will exhibit biological characteristics that distinguish the form from wild-type MurF activity, in which case the polymorphic form is also a mutant A protein or fragment thereof is considered purified or isolated when it is obtained at least partially free from it's natural environment in a composition or purity not found in nature. It is preferred that the molecule be present at a concentration at least about five-fold to ten-fold higher than that found in nature. A protein or fragment thereof is considered substantially pure if it is obtained at a concentration of at least about 100-fold higher than that found in nature. A protein or fragment thereof is considered essentially pure if it is obtained at a concentration of at least about 1000-fold higher than that found in nature. We most prefer proteins that have been purified to homogeneity, that is, at least 10,000–100,000 fold.

Probes and Primers

Polynucleotide probes comprising full length or partial sequences of SEQ ID NO:1 can be used to determine whether a cell or sample contains *P. aeruginosa* MurF DNA or RNA. The effect of modulators that effect the transcription of the murF gene can be studied via the use of these probes. A preferred probe is a single stranded antisense probe having at least the full length of the coding sequence of murF. It is also preferred to use probes that have less than the full length sequence, and contain sequences specific for *P. aeruginosa* murF DNA or RNA. The identification of a sequence(s) for user as a specific probe is well known in the art and involves choosing a sequence(s) that is unique to the target sequence, or is specific thereto. It is preferred that polynucleotides that are probes have at least about 25 nucleotides, more preferably about 30 to 35 nucleotides. The longer probes are believed to be more specific for *P. aeruginosa* murF gene(s) and RNAs and can be used under more stringent hybridization conditions. Longer probes can be used but can be more difficult to prepare synthetically, or can result in lower yields from a synthesis. Examples of sequences that are useful as probes or primers for *P. aeruginosa* murF gene(s) are Primer A (sense) 5'-TTTCATATGCTTGAGCCTCTTCGCCTC-3' (SEQ ID NO:3) and Primer B (antisense) 5'-TTGGATCCTTAGTGACTCTCCTCGGAG-3' (SEQ ID NO:4). These primers are nucleotides 1–21(A) and the complement of nucleotides 1358–1376 (B) respectively, of SEQ ID NO:1. Restriction sites, underlined, for NdeI and BamHI are added to the 5' ends of the primers to allow cloning between the NdeI and BamHI sites of the expression vector pET-15b. However, one skilled in the art will recognize that these are only a few of the useful probe or primer sequences that can be derived from SEQ ID NO:1.

Polynucleotides having sequences that are unique or specific for *P. aeruginosa* murF can be used as primers in amplification reaction assays. These assays can be used in tissue typing as described herein. Additionally, amplification reactions employing primers derived from *P. aeruginosa* murF sequences can be used to obtain amplified *P. aeruginosa* murF DNA using the murF DNA of the cells as an initial template. The murF DNA so obtained can be a mutant or polymorphic form of *P. aeruginosa* murF that differs from SEQ ID NO:1 by one or more nucleotides of the murF open reading frame or sequences flanking the ORF. The differences can be associated with a non-defective naturally occurring form or with a defective form of MurF. Thus, polynucleotides of this invention can be used in identification of various polymorphic *P. aeruginosa* murF genes or the detection of an organism having a *P. aeruginosa* murF gene. Many types of amplification reactions are known in the art and include, without limitation, Polymerase Chain Reaction, Reverse Transcriptase Polymerase Chain Reaction, Strand Displacement Amplification and Self-Sustained Sequence Reaction. Any of these or like reactions can be used with primers derived from SEQ ID NO:1.

Expression of MurF

A variety of expression vectors can be used to express recombinant MurF in host cells. Expression vectors are defined herein as nucleic acid sequences that include regulatory sequences for the transcription of cloned DNA and the translation of their mRNAs in an appropriate host. Such vectors can be used to express a bacterial gene in a variety of hosts such as bacteria, bluegreen algae, plant cells, insect cells and animal cells. Specifically designed vectors allow the shuttling of genes between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and regulatory sequences. A promoter is defined as a regulatory sequence that directs RNA polymerase to bind to DNA and initiate RNA synthesis. A strong promoter is one which causes mRNAs to be initiated at high frequency. Expression vectors can include, but are not limited to, cloning vectors, modified cloning vectors, specifically designed plasmids or viruses.

In particular, a variety of bacterial expression vectors can be used to express recombinant MurF in bacterial cells. Commercially available bacterial expression vectors which are suitable for recombinant MurF expression include, but are not limited to pQE (Qiagen), pET11a or pET15b (Novagen), lambda gt11 (Invitrogen), and pKK223-3 (Pharmacia).

Alternatively, one can express murF DNA in cell-free transcription-translation systems, or murF RNA in cell-free translation systems. Cell-free synthesis of MurF can be in batch or continuous formats known in the art.

One can also synthesize MurF chemically, although this method is not preferred.

A variety of host cells can be employed with expression vectors to synthesize MurF protein. These can include *E. coli*, *Bacillus*, and *Salmonella*. Insect and yeast cells can also be appropriate.

Following expression of MurF in a host cell, MurF polypeptides can be recovered. Several protein purification procedures are available and suitable for use. MurF protein and polypeptides can be purified from cell lysates and extracts, or from culture medium, by various combinations of, or individual application of methods including ultrafiltration, acid extraction, alcohol precipitation, salt fractionation, ionic exchange chromatography, phosphocellulose chromatography, lecithin chromatography, affinity (e.g., antibody or His-Ni) chromatography, size exclusion chromatography, hydroxylapatite adsorption chromatography and chromatography based on hydrophobic or hydrophillic interactions. In some instances, protein denaturation and refolding steps can be employed. High performance liquid chromatography (HPLC) and reversed phase HPLC can also be useful. Dialysis can be used to adjust the final buffer composition.

The MurF protein itself is useful in assays to identify compounds that modulate the activity of the protein—including compounds that inhibit the activity of the protein. The MurF protein is also useful for the generation of antibodies against the protein, structural studies of the protein, and structure/function relationships of the protein.

Modulators and Inhibitors of MurF

The present invention is also directed to methods for screening for compounds which modulate or inhibit a MurF protein. Compounds which modulate or inhibit MurF can be DNA, RNA, peptides, proteins, or non-proteinaceous organic or inorganic compounds or other types of molecules. Compounds that modulate the expression of DNA or RNA encoding MurF or are inhibitors of the biological function of MurF can be detected by a variety of assays. The assay can be a simple "yes/no" assay to determine whether there is a change in expression or function. The assay can be made quantitative by comparing the expression or function of a test sample with the levels of expression or function in a standard sample, that is, a control. A compound that is a modulator can be detected by measuring the amount of the MurF produced in the presence of the compound. An compound that is an inhibitor can be detected by measuring the specific activity of the MurF protein in the presence and absence of the compound.

The proteins, DNA molecules, RNA molecules and antibodies lend themselves to the formulation of kits suitable for the detection and analysis of MurF. Such a kit would comprise a compartmentalized carrier suitable to hold in close confinement at least one container. The carrier would further comprise reagents such as recombinant MurF or anti-MurF antibodies suitable for detecting MurP. The carrier can also contain a means for detection such as labeled antigen or enzyme substrates or the like.

Pharmaceutical Compositions

Pharmaceutically useful compositions comprising a modulator or inhibitor of MurF can be formulated according to known methods such as by the admixture of a pharmaceutically acceptable carrier. Examples of such carriers and methods of formulation can be found in Remington's Pharmaceutical Sciences. To form a pharmaceutically acceptable composition suitable for effective administration, such compositions will contain an effective amount of the inhibitor.

Therapeutic, prophylactic or diagnostic compositions of the invention are administered to an individual in amounts sufficient to treat, prevent or diagnose disorders. The effective amount can vary according to a variety of factors such as the individual's condition, weight, sex and age. Other factors include the mode of administration. The appropriate amount can be determined by a skilled physician The pharmaceutical compositions can be provided to the individual by a variety of routes such as subcutaneous, topical, oral and intramuscular.

The term "chemical derivative" describes a molecule that contains additional chemical moieties which are not normally a part of the base molecule. Such moieties can improve the solubility, half-life, absorption, etc. of the base molecule. Alternatively the moieties can attenuate undesirable side effects of the base molecule or decrease the toxicity of the base molecule. Examples of such moieties are described in a variety of texts, such as Remington's Pharmaceutical Sciences.

Compounds identified according to the methods disclosed herein can be used alone at appropriate dosages. Alternatively, co-administration or sequential administration of other agents can be desirable.

The present invention also provides a means to obtain suitable topical, oral, systemic and parenteral pharmaceutical formulations for use in the methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well known to those of ordinary skill in the pharmaceutical arts. Advantageously, compounds of the present invention can be administered in a single daily dose, or the total daily dosage can be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are presented by the way of illustration and, because various other embodiments will be apparent to those in the art, the following is not to be construed as a limitation on the scope of the invention. For example, while particular preferred embodiments of the invention are presented herein, it is within the ability of persons of ordinary skill in the art to modify or substitute vectors, host cells, compositions, etc., or to modify or design protocols or assays, all of which may reach the same or equivalent performance or results as the embodiments shown herein.

EXAMPLE 1

General Materials and Methods

All reagents were purchased from SIGMA CHEMICAL CO., St. Louis, Mo., unless otherwise indicated. UDP-N-acetylmuramyl-L-alanine was synthesized and purified by a method known in the art (Jin, H., Emanuele, J. J., Jr., Fairman, R., Robertson, J. G., Hail, M. E., Ho, H.-T., Falk, P. and Villafranca, J. J, 1996. Structural studies of *Escherichia coli* UDP-N-acetylmuramate: L-alanine ligase, Biochemistry 35: 14423–14431).

DNA Manipulations Reagents and Techniques.

Restriction endonucleases and T4 ligase were obtained from Gibco-BRL. Agarose gel electrophoresis and plasmid DNA preparations were performed according to published procedures (Sambrook, J., E. F. Fritsch, and T. Maniatis, 1989, Molecular cloning: a L, Laboratory Manual, 2nd ed. Cold Spring Harbor, N.Y.: Cold Spring Harbor Laboratory). Recombinant plasmids containing *P. aeruginosa* murF were propagated in *E. coli* DH5a (GIBCO-BRL, Rockville, Md.) prior to protein expression in *E. coli* BL21(DE3)/plysS (NOVAGEN, Madison, Wis.). SDS-PAGE was performed with precast gels (NOVAGEN). DNA sequences were determined using an automated ABI PRIS™ DNA sequencer (PERKIN-ELMER ABI, Foster City, Calif.).

EXAMPLE 2

Cloning of *Pseudomonas aeruginosa* murF

Genomic DNA from *P. aeruginosa* (strain MB4439) was prepared from 100 nml late stationary phase culture in Brain Heart Infusion broth (DIFCO, Detroit, W). Cells were washed with 0.2 M sodium acetate, suspended in 10 ml of TEG (100 mM Tris, pH 7, containing 10 mM EDTA and 25% glucose) and lysed by incubation with 200 µg of N-acetylmuramidase (SIGMA) for 1 h at 37° C. Chromosomal DNA was purified from the cell lysate using a QIAGEN (Santa Clarita, Calif.) genomic DNA preparation kit and following the manufacturers protocol. Briefly, the cell lysate was treated with protease K at 50° C. for 45 min, loaded onto an equilibrated QIAGEN genomic tip, entered into the resin by centrifugation at 3000 rpm for 2 min. Following washing the genomic tip, the genomic DNA was eluted in distilled water and kept at 4° C. Approximately 50 ng genomic DNA was used as a template in PCR reactions to clone murF.

Two oligonucleotide primers (GIBCO/BRL, Bethesda, Md.) complementary to sequences at the 5' and the 3' ends of *P. aeruginosa* murF were used to clone this gene using KLENTAQ ADVANTAG™ polymerase (CLONTECH, Palo Alto, Calif.). The primer nucleotide sequences were as follows: 5'-TTTCATATGCTTGAGCCTCTTCGCCTC-3' (SEQ ID NO:3) (a NdeI linker plus nucleotides 1–21 of SEQ ID NO:1) and 5'-TTGGATCCTTAGTGACTCTCCTCGGAG-3' (SEQ ID NO:4) (a BamHI linker plus the complement of nucleotides 1358–1376 of SEQ ID NO:1). A PCR product representing *P. aeruginosa* murF was verified by nucleotide sequence, digested with NdeI and BamHI, and cloned between the NdeI and BamHI sites of pET-I Sb, creating plasmid pPae-MurF. This plasmid was used for expression of the murF gene in *E. coli*.

EXAMPLE 3

Sequence Analysis of *Pseudomonas aeruginosa* murF

The nucleotide sequence of murF, determined in both orientations, and the deduced amino acid sequence of the MurF protein is depicted in FIG. 1. Sequence comparison using the BLAST (1) algorithm against the GenBank database showed that, to varying degrees, the cloned region is homologous (62% similar, 44% identical) to murF gene from *E. coli* (Parquet, C., D., Mengin-Lecreulx, B. Flouret, D. Mengin-lecreulx, and J. van Heijenoort, 1989. Nucleotide sequence of the murF gene encoding the UDP-MurNAc-pentapeptide synthetase of *Escherichia coli.*, Nucleic Acids Res. 17:5379).

EXAMPLE 4

Overexpression, Purification and Enzymatic Activity of *Pseudomonas aeruginosa* MurF murF was cloned into the expression vector pET-15b (Novagen) as described above to create plasmid pPaeMurF. The pET-15b vector incorporates the 6× Histidine-tag into the protein construct to allow rapid purification of MurF by affinity chromatography. The pET plasmids for Expression by T7 RNA polymerase) plasmids are derived from pBR322 and designed for protein over-production in E. coli. The vector pET-15b contains the ampicillin resistance gene, ColE1 origin of replication in addition to T7 phage promoter and terminator. The T7 promoter is recognized by the phage T7 RNA polymerase but not by the E. coli RNA polymerase. A host E coli strain such as BL21(DE3)pLysS is engineered to contain integrated copies of T7 RNA polymerase under the control of lacUV5 that is inducible by IPTG. Production of a recombinant protein in the E. coli strain BL21(DE3) pLysS occurs after expression of T7RNA polymerase is induced.

The pPaeMurF plasmid was introduced into the host strain BL21 DE3/pLysS (NOVAGEN) for expression of His-tagged MurF. Colonies were grown at 37° C. in 100 ml of LB broth containing 100 mg/ml ampicillin and 32 µg/ml chloramphenicol. When cultures reached a cell density of $A_{600}$=0.5, cells were pelleted and then resuspended in M9ZB medium (NOVAGEN) containing 1 mM IPTG. Cells were induced for 3 h at 30° C., pelleted at 3000g, and frozen at −80° C.

Cultures containing either the recombinant plasmid pPaeMurF or the control plasmid vector, pET-15b were grown at 30° C. and induced with IPTG. Cells transformed with pPaeMurF contained an inducible protein of approximately 51.6 kDa, corresponding to the expected size of P. aeruginosa MurF protein as shown by SDS-PAGE. There were no comparable detectable protein bands after induction of cells transformed with the control plasmid vector, pET-15b.
Purification of Recombinant MurF Enzyme.

The cell pellet from 100 ml of induced culture prepared as described above was resuspended in 10 ml BT buffer (50 mM bis-tris-propane, pH 8.0, containing 100 mM potassium chloride and 1% glycerol) at 4° C. Cells were lysed either by freeze-thaw or by French Press. After centrifugation, the supernatant was mixed with 15 ml of freshly prepared TALON (CLONTECH) resin and incubated for 30 min at room temp. The resin was washed twice by centrifugation with 25 ml of BT buffer at room temperature. Finally, the resin was loaded into a column and washed with 20 ml of BT, pH 7.0, containing 5 mM imidazole. Protein was eluted with 20 ml of BT buffer pH 8.0, containing 100 mM imidazole. Fractions (0.5 ml) were collected and analyzed by SDS-Gel electrophoresis. This resulted in a partially purified preparation of P. aeruginosa MurF protein that could be used in activity assays. The protein may be purified further, if desired, using methods known in the art.

The P. aeruginosa murF was cloned into pET-15b between the NdeI and the BamHI sites and expressed in E. coli strain BL21(DE3)/pLysS. The recombinant MurF enzyme was affinity purified and eluted in 100 mM imidazole. Aliquots from cell lysates, either uninduced or induced with IPTG, and column-purified polypeptides were analyzed by SDS-PAGE (FIG. 2).
Assay for Activity of MurF Enzyme.

The ATP-dependent MurF activity was assayed by monitoring the formation of product ADP using the pyruvate kinase and lactate dehydrogenase coupled enzyme assay. The reaction was monitored spectrophotometrically.

Typically, the assay contained 100 mM BIS-TRIS-propane, pH 8.0, 200 µM NADH, 1 mM ATP, 20 mM PEP, 5 MM $MgCl_2$, 1 mM DTT, 350 µM UDP-N-acetyl-muramyl-L-alanine-D-Glutamine-m-Dap, 1 mM D-alanine-D-alanine, 33 units/ml of pyruvate kinase and 1660 units/ml of lactate dehydrogenase in a final volume of 200 or 400 µl. The mixture was incubated at 25° C. for 5 min and the reaction initiated by the addition of ~10 µg of MurF. These conditions are one example of an assay useful for evaluating the activity of MurF. Other assays can be used, or amounts of buffers, substrate and enzyme can be changed, as desired, to alter the rate of production of ADP.

ADP formation was monitored by the decrease in absorbance at 340 nm as a function of time using a SPECTRAMAXPLUS (MOLECULAR DEVICES) microtiterplate spectrophotomer (for 200 µl assays) or a HEWLETT-PACKARD HP8452A spectrophotometer equipped with a circulating water bath (for 400 µl assays). Rates were calculated from the linear portions of the progress curves using the extinction coefficient for NADH, e=6220 cm$^{-1}$ M$^{-1}$. One unit of MurF activity is equal to 1 µmol of ADP formed per min at 25° C. MurF activity co-eluted with a ~51 kDa protein.

TABLE 1

Specific activities of recombinant MurF from E. coli and P. aeruginosa.

| Mur Ligase | P. aeruginosa µmol × min$^{-1}$ × mg$^{-1}$ | E. coli µmol × min$^{-1}$ × mg$^{-1}$ |
|---|---|---|
| MurF | 3.41 | 1.15 |

EXAMPLE 5
Screening for Inhibitors of MurF

One assay for the measurement of the activity of MurF is provided in Example 4. That assay, and other assays for MurF activity can be adapted for screening assays to detect inhibitors of MurF. For example, for inhibition assays, inhibitors in DMSO are added at the desired concentration to the assay mixture. In a separate, control reaction, only DMSO is added to the assay mixture. The reactions are initiated by the addition of enzyme (MurF). Rates are calculated as described above. Relative activities are calculated from the equation 1:

$$\text{relative activity=rate with inhibitor/rate without inhibitor.} \quad (1)$$

Inhibition constant ($IC_{50}$) values are determined from a range of inhibitor concentrations and calculated from equation 2.

$$\text{relative activity} = 1/(1+[I]/IC_{50}) \quad (2)$$

One can use computer software to assist in the analysis, e.g., SIGMA PLOT™ (JANDEL SCIENTIFIC, San Rafeal).

We prefer inhibitors of MurF that result in relative activities of the MurF enzyme of at least less than 75%, more preferably, 25–50% or 10–25%. We most prefer inhibitors resulting in relative activities of less than 20%, particularly less than 10% of the activity of MurF in the absence of the inhibitor.

We also prefer inhibitors that effectively lower the relative activity of MurF when the inhibitor is present at a very low concentration.

EXAMPLE 8
Therapy using Inhibitors of MurF

A patient presenting with an indication of infection with a microorganism susceptible to inhibitors of MurF, e.g., gram positive and negative bacteria, including *P. aeruginosa*, can be treated by administration of inhibitors of MurF. Physicians skilled in the art are familiar with administering therapeutically effective amounts of inhibitors or modulators of microbial enzymes. Such skilled persons can readily determine an appropriate dosing scheme to achieve a desired therapeutic effect.

Therapy can also be prophylactic. For example, a patient at risk for developing a bacterial infection, including infection with *P. aeruginosa*, can be treated by administration of inhibitors of MurF. Physicians skilled in the art are familiar with administering therapeutically effective amounts of inhibitors or modulators of microbial enzymes. Such skilled persons can readily determine an appropriate dosing scheme to achieve a desired therapeutic effect.

What is claimed:

1. A purified and isolated polynucleotide selected from the group consisting of:
   (a) a polynucleotide encoding a polypeptide having the amino acid sequence of SEQ ID NO: 2, and
   (b) a polynucleotide which is complementary to the polynucleotide of (a).

2. The polynucleotide of claim 1 wherein the polynucleotide comprises nucleotides selected from the group consisting of natural, non-natural and modified nucleotides.

3. The polynucleotide of claim 1 wherein the internucleotide linkages are selected from the group consisting of natural and non-natural linkages.

4. The polynucleotide of claim 1 comprising the nucleotide sequence of SEQ ID NO:1.

5. An expression vector comprising a polynucleotide encoding a polypeptide having the amino acid sequence of SEQ ID NO:2.

6. A host cell comprising the expression vector of claim 5.

7. A process for expressing a MurF protein of *Pseudomonas aeruginosa* in a recombinant host cell, comprising:
   (a) transforming a suitable host cell with an expression vector of claim 5; and
   (b) culturing the host cell of step (a), under conditions which allow expression of said the MurF protein from said expression vector.

8. A purified and isolated polypeptide having the amino acid sequence of SEQ ID NO:2.

9. A method of determining whether a candidate compound is an inhibitor of a *Pseudomonas aeruginosa* MurF polypeptide comprising:
   (a) providing at least one host cell harboring an expression vector that includes a polynucleotide encoding a polypeptide having the amino acid sequence of SEQ ID NO: 2,
   (b) contacting at least one of said cells with the candidate to permit the interaction of the candidate with the MurF polypeptide, and
   (c) determining whether the candidate is an inhibitor of the MurF polypeptide by ascertaining the relative activity of the polypeptide in the presence of the candidate.

10. The method of claim 9 wherein the polynucleotide has the nucleotide sequence of SEQ ID NO:1.

11. The method of claim 9 wherein in step (c) the relative activity is determined by comparing a measurement of MurF polypeptide activity of at least one cell before step (b) to a measurement of MurF polypeptide activity of at least one cell after step (b).

12. A method of determining whether a candidate compound is an inhibitor of a *Pseudomonas aeruginosa* MurF polypeptide comprising:
   (a) providing a sample that includes a MurF polypeptide having the amino acid sequnece of SEQ ID NO: 2,
   (b) contacting said sample with the candidate to permit the interaction of the candidate with the MurF polypeptide, and
   (c) determining whether the candidate is an inhibitor of the MurF polypeptide by ascertaining the relative activity of the MurF polypeptide in the presence of the candidate.

13. The method of claim 12 wherein in step (c) the relative activity is determined by comparing a measurement of MurF polypeptide activity of the sample before step (b) to a measurement of MurF polypeptide activity of the sample after step (b).

* * * * *

SEQUENCE LISTING

<160> NUMBER OF SEQ ID NOS: 4

<210> SEQ ID NO 1
<211> LENGTH: 1449
<212> TYPE: DNA
<213> ORGANISM: Pseudomonas aeruginosa

<400> SEQUENCE: 1

```
tccgttctcc gacatcgagc aggccgagcg cgccctggcc gcctgggagg tgccgcatgc      60
ttgagcctct tcgcctcagc cagttgacgg tcgcgctgga cgcccgcctg atcgcgagg     120 acgccgtctt ttcggcggtt tccaccgaca gtcgcgccat cgggcccggc caactgttca    180
ttgccctgag tgggccgcgt ttcgacgcc acgactatct cgccgaggtt gccgccaagg     240
gcgcggtggc tgcgctggtg gagcgcgaag tcgccgacgc gcccttgccg caattgctgg    300
tgcgcgatac ccgtgcggcc ctgggcgac tgggcgcgct gaaccggcgc aagttcaccg     360
gcccgctggc ggccatgacg ggctccagcg gcaagaccgc ggtcaaggag atgctcgcca    420
gcatcctgcg tacccaggcc ggcgatgccg agtcggtgct ggctacccgt ggcaatctga    480
acaacgacct cggcgtaccg ctgaccctgc tgcaactggc gccgcagcac cgtagcgcag    540
tgatcgaact gggcgcctcg cgcatcgcg agatcgccta cacggtcgag ctgacccgcc     600
cgcacgtggc gatcatcacc aatgccggaa ccgcccatgt cggcgagttc ggcggaccgg    660
agaagatcgt cgaggcgaag ggcgagatac tcgaagggct ggccgccgac ggcaccgccg    720
tactgaacct ggacgacaag gccttcgaca cctggaaggc ccgtgccagc ggccgtccgt    780
tgctgacttt ctccctcgac cggccccagg ccgatttccg cgccgccgat ctgcagcgcg    840
atgcgcgcgg ctgcatgggc ttcaggctgc agggcgtagc gggtgaagcg caggtccagc    900
tcaacctgct ggggcggcac aatgtcgcca atgccctggc tgcggccgct gccgcccatg    960
cactgggcgt gccgctggat gggatcgtcg ccgggctgca ggcgctgcag ccggtcaagg   1020
gccgcgcggt agcgcaactg accgccagcg ggctgcgtgt gatagacgac agctacaacg   1080 ccaacccgc gtcaatgctg gcggcgattg atatactgag cggcttttcc gggcgcaccg    1140
tcctggtcct cggagacatg ggcgaactcg gttcctgggc cgagcaggcc caccgcgagg   1200
tgggcgccta cgccgctggc aaggtgtccg cgctctatgg ggtcggaccg ctgatggccc    1260
acgccgtaca ggcgttcggc gccacgggcc ggcacttcgc cgaccaggcc agcctgatcg   1320
gggcgctggc caccgaacaa ccgacaacca ccatttttgat caagggttcc cgcagtgcgg   1380
cgatggacaa agtcgtcgcg gcgctgtgcg gttcctccga ggagagtcac taatgctcct   1440
gctgctggc                                                          1449
```

<210> SEQ ID NO 2
<211> LENGTH: 458
<212> TYPE: PRT
<213> ORGANISM: Pseudomonas aeruginosa

<400> SEQUENCE: 2

```
Met Leu Glu Pro Leu Arg Leu Ser Gln Leu Thr Val Ala Leu Asp Ala
 1               5                  10                  15

Arg Leu Ile Gly Glu Asp Ala Val Phe Ser Ala Val Ser Thr Asp Ser
                20                  25                  30

Arg Ala Ile Gly Pro Gly Gln Leu Phe Ile Ala Leu Ser Gly Pro Arg
            35                  40                  45

Phe Asp Gly His Asp Tyr Leu Ala Glu Val Ala Ala Lys Gly Ala Val
        50                  55                  60

Ala Ala Leu Val Glu Arg Glu Val Ala Asp Ala Pro Leu Pro Gln Leu
65                  70                  75                  80

Leu Val Arg Asp Thr Arg Ala Ala Leu Gly Arg Leu Gly Ala Leu Asn
                85                  90                  95

Arg Arg Lys Phe Thr Gly Pro Leu Ala Ala Met Thr Gly Ser Ser Gly
                100                 105                 110

Lys Thr Ala Val Lys Glu Met Leu Ala Ser Ile Leu Arg Thr Gln Ala
            115                 120                 125

Gly Asp Ala Glu Ser Val Leu Ala Thr Arg Gly Asn Leu Asn Asn Asp
130                 135                 140

Leu Gly Val Pro Leu Thr Leu Leu Gln Leu Ala Pro Gln His Arg Ser
145                 150                 155                 160

Ala Val Ile Glu Leu Gly Ala Ser Arg Ile Gly Glu Ile Ala Tyr Thr
                165                 170                 175

Val Glu Leu Thr Arg Pro His Val Ala Ile Ile Thr Asn Ala Gly Thr
                180                 185                 190

Ala His Val Gly Glu Phe Gly Gly Pro Glu Lys Ile Val Glu Ala Lys
            195                 200                 205

Gly Glu Ile Leu Glu Gly Leu Ala Ala Asp Gly Thr Ala Val Leu Asn
210                 215                 220

Leu Asp Asp Lys Ala Phe Asp Thr Trp Lys Ala Arg Ala Ser Gly Arg
225                 230                 235                 240

Pro Leu Leu Thr Phe Ser Leu Asp Arg Pro Gln Ala Asp Phe Arg Ala
                245                 250                 255

Ala Asp Leu Gln Arg Asp Ala Arg Gly Cys Met Gly Phe Arg Leu Gln
                260                 265                 270

Gly Val Ala Gly Glu Ala Gln Val Gln Leu Asn Leu Leu Gly Arg His
            275                 280                 285

Asn Val Ala Asn Ala Leu Ala Ala Ala Ala Ala His Ala Leu Gly
            290                 295                 300

Val Pro Leu Asp Gly Ile Val Ala Gly Leu Gln Ala Leu Gln Pro Val
305                 310                 315                 320

Lys Gly Arg Ala Val Ala Gln Leu Thr Ala Ser Gly Leu Arg Val Ile
            325                 330                 335

Asp Asp Ser Tyr Asn Ala Asn Pro Ala Ser Met Leu Ala Ala Ile Asp
            340                 345                 350

Ile Leu Ser Gly Phe Ser Gly Arg Thr Val Leu Val Leu Gly Asp Met
            355                 360                 365

Gly Glu Leu Gly Ser Trp Ala Glu Gln Ala His Arg Glu Val Gly Ala
        370                 375                 380

Tyr Ala Ala Gly Lys Val Ser Ala Leu Tyr Ala Val Gly Pro Leu Met
385                 390                 395                 400

Ala His Ala Val Gln Ala Phe Gly Ala Thr Gly Arg His Phe Ala Asp
                405                 410                 415
```

```
Gln Ala Ser Leu Ile Gly Ala Leu Ala Thr Glu Gln Pro Thr Thr Thr
            420                 425                 430

Ile Leu Ile Lys Gly Ser Arg Ser Ala Ala Met Asp Lys Val Val Ala
        435                 440                 445

Ala Leu Cys Gly Ser Ser Glu Glu Ser His
    450                 455

<210> SEQ ID NO 3
<211> LENGTH: 27
<212> TYPE: DNA
<213> ORGANISM: Artificial Sequence
<220> FEATURE:
<223> OTHER INFORMATION: PCR Primer

<400> SEQUENCE: 3
tttcatatgc ttgagcctct tcgcctc                                    27

<210> SEQ ID NO 4
<211> LENGTH: 27
<212> TYPE: DNA
<213> ORGANISM: Artificial Sequence
<220> FEATURE:
<223> OTHER INFORMATION: PCR Primer

<400> SEQUENCE: 4
ttggatcctt agtgactctc ctcggag                                    27
```